United States Patent
Das et al.

(10) Patent No.: US 9,909,100 B2
(45) Date of Patent: Mar. 6, 2018

(54) PLANT EXTRACT BASED COMPOSITION USEFUL FOR LEISHMAN IA PROMASTIGOTES

(71) Applicant: Indian Council of Medical Research, New Delhi (IN)

(72) Inventors: Pradeep Das, Patna (IN); Anil Kumar Gupta, Patna (IN)

(73) Assignee: Indian Council of Medical Research (IN)

( * ) Notice: Subject to any disclaimer, the term of this patent is extended or adjusted under 35 U.S.C. 154(b) by 0 days.

(21) Appl. No.: 14/770,984

(22) PCT Filed: Apr. 25, 2014

(86) PCT No.: PCT/IN2014/000270
§ 371 (c)(1),
(2) Date: Aug. 27, 2015

(87) PCT Pub. No.: WO2014/174533
PCT Pub. Date: Oct. 30, 2014

(65) Prior Publication Data
US 2016/0010053 A1      Jan. 14, 2016

(30) Foreign Application Priority Data

Apr. 26, 2013 (IN) .......................... 1233/DEL/2013

(51) Int. Cl.
*C12N 1/10* (2006.01)

(52) U.S. Cl.
CPC ..................................... *C12N 1/10* (2013.01)

(58) Field of Classification Search
None
See application file for complete search history.

(56) References Cited

PUBLICATIONS

Delorenzi et al., Antileishmanial Activity of an Indole Alkaloid from Peschiera australis, Antimicrobial Agents and Chemotherapy, May 2001, pp. 1349-1354.*
Schneider's Insect Medium (last visited on Dec. 12, 2015).*
Potdar et al., Evaluation of Antidepressant-like Effect of Citrus Maxima Leaves in Animal Models of Depression, Iranian Journal of Basic Medical Sciences, vol. 14, No. 5, Sep.-Oct. 2011, 478-483.*
Sigma Aldrich, Product Information, pp. 1-2.*
Melo et al., "A new defined medium for cultivating "Leishmania" promastigotes," Acta Tropica, (1985), vol. 42, pp. 137-141.
Ozbilgin, et al., "Cultivation of *Leishmania* sp. in nutrient broth.," J. Egypt Soc. Parasitol, (Aug. 1995), vol. 25, No. 2, pp. 437-441. (Abstract Only).
Dietz et al., "Actinomycetes," Maintaining Cultures for Biotechnology and Industry, (1996), pp. 85-99.
Mazyad et al., "Peptone-liver (P-L) a new culture medium for the Egyptian Leishmania major," J. Egypt Soc. Parasitol, (Apr. 2003), vol. 33, No. 1, pp. 41-45. (Abstract Only).
Mbati et al., "Establishment of an appropriate inoculum dose of Leishmania donovani promastigotes required to establish a visceral infection in laboratory animal rodent models," Afr. J. Health Sci., (Nov. 1994), vol. 1, No. 4, pp. 165-168. (Abstract Only).
Aljeboori, T.I., A simple diphasic medium lacking whole blood for culturing *Leishmania* spp., Transactions of the Royal Society of Tropical Medicine and Hygiene, (1979), vol. 73, No. 1, p. 117.
Agarwal et al., "New blood free biphasic medium with haemoglobin for cultivation of Leishmania donovani promastigotes," Indian Journal of Experimental Biology, (Dec. 1996), vol. 34, pp. 1233-1236.
Gupta et al., "Blood-Based Autoclavable Medium for In-Vitro Cultivation of Leishmania Donovani Promastigotes," Indian J. Comp. Microbiol. Immunol. Infect. Dis., (Jul. & Oct. 1995), vol. 16, Nos. 3 & 4, pp. 144-145.
Gupta et al., "In-Vitro Maintenance of Leishmania donovani Promastigotes in a Cheap, Serum-free, Hemin-based Autoclavable Culture Medium," J. Com. Dis., (1991), vol. 23, No. 4, pp. 276-277.
Bhattacharya et al., "A simple medium without blood modified for successful isolation & cultivation of LD bodies," Indian J. Med. Res., (Apr. 1994), vol. 99, pp. 171-172.
Ali et al., "A Semisynthetic Fetal Calf Serum-Free Liquid Medium for In Vitro Cultivation of Leishmania Promastigotes," Am. J. Trop. Med. Hyg., (1998) vol. 59, No. 1, pp. 163-165.
Beattie et al., "Trehalose: A Cryoprotectant That Enhances Recovery and Preserves Funtion of Human Pancreatic After Long-Term Storage," Diabetes, (Mar. 1997), vol. 46, pp. 519-523.
Armstrong et al., "Cultivation of Leishmania braziliensis in an Economical Serum-Free Medium Containing Human Urine," The Journal of Parasitology, (Dec. 1994), vol. 80, No. 6, pp. 1030-1032.
Berens et al., "A Simple Monophasic Medium for Axenic Culture of Hemoflagellates," The Journal of Parasitology, (Jun. 1976), vol. 62, No. 3, pp. 360-365.
Bhattacharyya et al., "Studies on Stibanate unresponsive isolates of Leishmania donovani," J. Biosci., (Sep. 2002), vol. 27, No. 5, pp. 503-508.
Ramachandra et al., "Liver Freezing Response of the Freeze-Tolerant Wood Frog, *Rana sylvatica* in the Presence and Absence of Glucose," Cryobiology, (1999), vol. 38, pp. 310-326.
Chang et al., "Heme Requirement and Acquisition by Extracellular and Intracellular Stages of Leishmania Mexicana Amazonensis," Molecular and Biochemical Parasitology, (1985), vol. 16, pp. 267-276.
Berens et al., "An Easily Prepared Defined Medium for Cultivation of Leishmania donovani Promastigotes," The Journal of Parasitology, (Feb. 1978), vol. 64, No. 1, p. 160.
Chaudhuri, et al., "Growth factor requirements for in vitro growth of Leishmania donovani," Indian J. Med. Res., (Jul. 1982), vol. 76, pp. 157-163.
Chaudhuri et al., "Nutrition of Leishmania donovani donovani: Growth in new semidefined & completely chemically defined media," Indian J. Med. Res., (Nov. 1986), vol. 84, pp. 461-468.
Chaudhuri et al., "A new medium for large scale production of Leishmania donovani promastigotes for biochemical studies," Indian J. Med. Res., (Nov. 1986), No. 84, pp. 457-460.

(Continued)

*Primary Examiner* — Suzanne M Noakes
*Assistant Examiner* — Stephen Chong
(74) *Attorney, Agent, or Firm* — The Webb Law Firm

(57) ABSTRACT

This invention relates to a culture medium for cultivation of *Leishmania* promastigotes, comprising inorganic salts, organic constituents and peptone/hydrolystate and at least one plant extract.

9 Claims, No Drawings

(56) References Cited

PUBLICATIONS

Giannini, M.S., "Effects of Promastigote Growth Phase, Frequency of Subculture, and Host Age on Promastigote-initiated Infections with Leishmania donovani in the Golden Hamster," J. Protozool., (1974), vol. 21, No. 4, pp. 521-527.

Desjeux, P., M.D., "Leishmaniasis Public Health Aspects and Control," Clinics in Dermatology, (1996), vol. 14, pp. 417-423.

Dey et al., "Infectivity and Virulence of Leishmania donovani Promastigotes: A Role for Media, Source, and Strain of Parasite," J. Eukaryat. Microbiol., (2002), vol. 49, No. 4, pp. 270-274.

Eroglu et al., "Intracellular trehalose improves the survival of cryopreserved mammalian cells," Nature Biotechnology, (Feb. 2000), vol. 18, pp. 163-167.

Evans, D.A., An inexpensive easily available replacement for foetal calf serum in media for the in vitro cultivation of *Leishmania* spp., Z-Parasitenkunde, (1986) vol. 72, pp. 567-572.

Enders et al., "Biochemical and technical considerations regarding the mass production of certain parasitic protozoa," Bulletin of the World Health Organization, (1977), vol. 55, Nos. 2-3, pp. 391-402.

Fuente et al., "A liquid modification of Difco Blood Agar medium for cultivation of Leishmania," Transaction of the Royal Society of Tropical Medicine and Hygiene, (1983), vol. 77, No. 6, p. 882.

Bagirova et al., "Effect of cell-conditioned media on biomass production of Leishmania parasites," Turk J. Biol., (2012) vol. 36, pp. 653-657.

Hill et al., "*Leishmania* spp.: Agar Plating as an Alternative to Limiting Dilution and Impression Smears for the Enumeration of Viable Parasites in Tissue," Experimental Parasitology, (1987), vol. 63, pp. 108-111.

Hendricks et al., "Haemoflagellates: commercially available liquid media for rapid cultivation," Parasitology, (1978), vol. 76, pp. 309-316.

Handman et al., "Isolation and Characterization of Infective and Non-Infective Clones of Leishmania Tropica," Molecular and Biochemical Parasitology, (1983), vol. 7, pp. 111-126.

Habtemariam, S., "Cytoxic and Cytostatic activity of erlangerins from Commiphora erlangeriana," Toxicon, (2003), vol. 41, pp. 723-727.

Kar et al., "Leishmania donovani: A Chemically Defined Medium Suitable for Cultivation and Cloning of Promastigotes and Transformation of Amastigotes to Promastigotes," J. Protozool., (1990), vol. 37, No. 4, pp. 277-279.

Ali et al., "In vitro maintenance of Leishmania promastigote in an egg based biphasic culture medium," Methods in Cell Science, (1997), vol. 19, pp. 107-110.

Steiger et al., "A Defined Medium for Cultivating Leishmania donovani and L. braziliensis," The Journal of Parasitology, (Dec. 1976), vol. 62, No. 6, pp. 1010-1011.

Steiger et al., "Cultivation of Leishmania donovani and Leishmania braziliensis in Defined Media: Nutritional Requirements," J. Protozool., (1977), vol. 24, No. 3, pp. 437-441.

Wagner et al., "Leishmania tarentolae: Streptomycin and Chloramphenicol Resistance of Promastigotes," Experimental Parasitology, (1976), vol. 39, pp. 222-233.

Iovannisei et al., "High Efficiency Plating Method for Leishmania Promastigotes in Semidefined or Completely-Defined Medium," The Journal of Parasitology, (Aug. 1983), vol. 69, No. 4, pp. 633-636.

Pal et al., "Dose-dependent differential effect of hemin on protein synthesis and cell proliferation in Leishmania donovani promastigotes cultured in vitro," J. Biosci., (Jun. 2001), vol. 26, No. 2, pp. 225-231.

Keppel et al., "Morphology of Leishmania donovani Colonies Grown on Blood Agar Plates," The Journal of Parasitology, (Oct. 1980), vol. 66, No. 5, pp. 849-851.

Lemesre et al., "Requirements of defined cultivation conditions for standard growth of Leishmania promastigotes in vitro," Acta Tropica, (1988) vol. 45, pp. 99-108.

Limoncu et al., "A New Experimental In Vitro Culture Medium for Cultivation of Leishmania Species," Journal of Clinical Microbiology, (Sep. 1997), vol. 35, No. 9, pp. 2430-2431.

Merlen et al., "*Leishmania* spp.: Completely Defined Medium Without Serum and Macromolecules (CDM/LP)for the Continuous In Vitro Cultivation of Infective Promastigote Forms," Am. J. Trop. Med. Hyg., (1999), vol. 60, No. 1, pp. 41-50.

O'Daly et al., "Differential growth requirements of several "*Leishmania* " spp. in chemically defined culture media," Acta Tropica, (1988), vol. 45, pp. 109-126.

Newman, C., "Serum-free cell culture—the ethical, scientific and economic choice," The Biomedical Scientist, (Sep. 2003), pp. 941-942.

Pal et al., "Studies on stibanate resistant Leishmania donovani isolates of Indian origin," Indian Journal of Experimental Biology, (Mar. 2001), vol. 39, pp. 249-254.

Schlein et al., "Mortality of Leishmania Major in Phlebotomus Papatasi Caused by Plant Feeding of the Sand Flies," Am. J. Trop. Med. Hyg., (1994), vol. 50, No. 1, pp. 20-27.

Shamsuzzaman et al., "Use of urine samples from healthy humans, nephritis patients or other animals as an alternative to foetal calf serum in the culture of Leishmania (L.) donovani in vitro," Annals of Tropical Medicine & Parasitology, (1999), vol. 93, No. 6, pp. 613-620.

Simpson, L., "The Leishmania-Leptomonad Transformation of Leishmania donovani: Nutritional Requirements, Respiration Changes and Antigenic Changes,", J. Protozool., (1968), vol. 15, No. 1, pp. 201-207.

Soteriadou et al., "Effect of iron chelation on the in-vitro growth of leishmania promastigotes," Journal of Antimicrobial Chemotherapy, (1995), vol. 35, pp. 23-29.

\* cited by examiner

PLANT EXTRACT BASED COMPOSITION USEFUL FOR LEISHMAN IA PROMASTIGOTES

CROSS-REFERENCE TO RELATED APPLICATIONS

This application is the United States national phase of International Application No. PCT/IN2014/000270 filed Apr. 25, 2014, and claims priority to Indian Patent Application No. 1233/DEL/2013 filed Apr. 26, 2013, the disclosures of which are hereby incorporated in their entirety by reference.

FIELD OF THE INVENTION

This invention relates to a plant extract based culture medium useful for *Leishmania* promastigotes. More particularly, the present invention relates to a culture medium having composition essentially comprising plant extract useful for growth of *Leishmania* promastigotes, a parasitie haemoflagellate of human interest.

PRIOR ART OF THE INVENTION

Leishmaniasis is a disease spread over tropical and subtropical region of 88 countries (W.H.O., 1998. *Leishmania* and HIV in grid lock. WHO/UNAIDS report. Geneva: World Health Organization. 15-25). Among which, 16 are developed countries, 72 developing countries and 13 least developed (Desjeux P, 1996. Leishmaniasis: public health aspects and control. Clin. Dermatol. 14: 417-423). It is caused by members of hemoflageilate protozoan parasites of the genus *Leishmania* and is transmitted by the bite of female phlebotomine sandflies. The parasite undergoes a digenic life cycle between a nonmotile intracellular amastigote stage parasitizing the mammalian phagocytic cells and a flagellated, motile promastigote stage in the midgut of its sandfly vector (Adler S, 1964. *Leishmania*. Dawes B, ed. *Advances in Parasitology*. Volume 2. New York: Academic Press, Inc., 35-96). A similar promastigote form develops when parasites are cultured in cell-free medium. *Leishmania* spp. do not have heme-biosynthetic pathway and require exogenous heme as essential growth factor from serum/blood/blood products present in immediate environment for growth and multiplication (Chang, C. S. and Chang, K. P. 1985. Heme requirement and acquisition by extracellular and intracellular stages of *Leishmania mexicana amazonensis*. Mol. Biochem. Parasitol. 16: 267-276; Soteriadou, K., Papavassiliou, P., Voyiatzaki, C., Boelaert, J., 1995. Effect of iron chelation on the in-vitro growth of *Leishmonio* promastigotes. J. Antimicrob. Chemother 35, 23-29). Therefore, a medium containing heme substances e.g. blood/a blood product is required for culturing *Leishrnotvo* promastigotes.

Since the beginning of 20th century, cultivation of the *Leishmonio* developed with NNN medium (the Novy-Mc Neal (1904) medium, as modified by Nicolle (1908)), which consist blood agar slant inoculated with infected materials. Till then, the modifications in NNN medium especially in the basal phase are being carried out, which involve replacement of the bacto-agar with richer nutrient agars (i.e. Difco blood-agar, Walton B C, Shaw J J and Lainson R, 1977. Observations on the in vitro cultivation of *Leishmonio braziliensis*. J. Parasitol. 63:1118-1119; brain heart infusion agar, Marin F, De Lomas, J G, Penarrubia M P G and Penaluer J. 1982. Cultivation of *Leishmonio*: comparison of different media for promastigotes cultivation. Ann. Trop. Med. Parasitol. 76: 607-613; various tissue extracts, or serum plasma Weinman, 1960. Trans. Roy. Soc. trop. Med. Hyg., 54, 180) has also been tested.

Several semi-defined/defined and biphasic/monophasic media have been developed for the cultivation of different species or sub-species of *Leishmonio* parasites (Steiger R F and Steiger E., 1976. A defined medium for cultivating *Leishmonio donovoni* and *L braziliensis*. J. Parasitol. 62: 1010-1011; Steiger R F and Steiger E, 1977. Cultivation *Leishmonio donovoni* and *L. Braziliensis* in defined media: nutritional requirements. J. Protozool. 24(3): 437-441; Berens, R. L. and Marr, J. J. 1978. An easily prepared defined medium for cultivation of *Leishmonio donovoni* promastigotes. J. Parasitol. 64: 160-167; Dumon H, Manoury B, Quilici M and Ranque J, 1981. Growth of *Leishmonio infantum* in continuous culture. C R. Seances Soc. Biol. Fil. 175 (1): 82-86; Chaudhary, G., Chatterjee, T. K. and Banerjee, A. B., 1982. Growth factor requirements for in vitro growth of *Leishmonio donovoni*, Indian J. Med. Res. 76: 157-163.; La Fuente C, Saucedo E and Urjel R, 1983. A liquid modification of Difco Blood Agar medium for cultivation of *Leishmonio*. Trans. R. Soc. Trop Med Hyg. 77 (6): 882; Melo N M, De Azevedo H P, Roitman I, Mayrink W, 1985. A new defined medium for cultivating *Leishmonio* promastigotes. Acta Trop. 42(4): 137-141; Chaudhary G, Ghoshal K, Sen S, Pal S and Banerjee A B, 1986. Nutrition of *Leishmonio donovoni donovoni*: Growth in new semi defined & completely chemically defined media. Indian J. Med. Res. 84: 461-468; O'Daly J A and Rodriguez M B, 1988. Differential growth requirements of several *Leishmonio* spp. in chemically defined culture media. Acta Trop. 45(2): 109-126; Gupta A K and Saran R, 1991. In vitro maintenance of *Leishmonio donovoni* promastigotes in a cheap, serum-free, hemin-based, autoclavable culture medium. J. Commun. Dis. 23: 276-2 77; Mc Carthy-Burke C, Bates P and Dwyer D M, 1991. *Leishmonio donovoni*: use of two different, commercially available, chemically defined media for continuous in vitro cultivation of promastigotes; Exp. Parasitol. 73 (3): 385-387; Ozbilgin A, Ozbel Y, Alkan M Z, Atambay, M, Ozcel M A, 1995. Cultivation of *Leishmonio* sp. in nutrient broth. *J Egypt Soc Parasitol* 25: 437-41; Lozano J, Campos M, Manas I and Diaz V, 1996. Semi-defined medium for cultivating *Leishmanio infantum* promastigotes. Ars. Pharm. 37 (3): 563-567; Limoneu M E, Balcioglu C, Yereli K, Ozbel Y and Ozbilgin A, 1997. A new experimental in-vitro culture medium for cultivation of *Leishmanio* species. Journal of Clinical Microbiology. 35 (9) 2 430-2431; AN et al., 1998; Merlen T, Sereno D, Brajon N, Rostand F and Lemesre J L, 1999. *Leishmanio* spp: completely defined medium without serum and macromolecules (CDM/LP) for continuous in-vitro cultivation of infective promastigotes forms. Am. J. Trop. Med. Hyg. 60: 41-50; Mazyad S A and. Abdel-Aziz A, 2003. Peptone-liver (P-L) a new culture medium for the Egyptian *Leishmanio major*. J. Egypt. Soc. Parasitol. 33 (1): 41-45.

Presently, all the basal culture media either semi-defined/defined, formulated or based upon commercial tissue culture media need supplementation of animal-derived products such as blood (chiefly pooled fresh rabbit blood at concentrations ca. 2.5 to 30%) or FCS (at ca. 5 to 30%), or adult serum (Evans D A, 1986. An inexpensive easily available replacement for foetal calf serum in media for the in vitro cultivation of *Leishmanio* spp. 7 *Parasitenkd* 72: 567-572), or blood products i.e. hemin or hemoglobin (Aljeboori T I, 1979. A simple biphasic medium lacking whole blood for culturing *Leishmanio* spp. Trans. R. Soc. Trop. Med. Hyg. 73 (1): 117; Gupta A K and Saran R, 1991. In vitro maintenance of *Leishmanio donovani* promastigotes in a cheap, serum-free, hemin-based, autoclavable culture medium. J. Commun. Dis. 23: 276-277; Bhattacharya, J., Mukharjee, H., Das, D. C. and Hati, A. K. (1994) A simple medium without blood modified for successful isolation and cultivation of LD bodies. Indian J. Med. Res. 99: 171-172; Gupta A K, Narayan S and Saran R, 1995. Blood-based autoclavable medium for in-vitro cultivation of *Leishmonia donovoni* promastigotes. Indian J. Comp. Microbiol. Immunol. Infect. Dis. 16 (3-4): 144 145; Agarwal M and Jain A, 1996. New blood free biphasic medium with haemoglobin for cultivation of *Leishmonia donovani* promastigotes. Indian J. Exp. Biol. 34 (12): 1233-1236) or may also involve bovine serum albumin, peptone, infusion, extract.

The culture media designed specifically for *Leishmanio* cultivation contain either fetal calf serum (FCS) or blood lysate as one of their essential ingredients (Hendricks L D and Childs G E, 1980. Present knowledge of the in vitro cultivation of *Leishmonia*. The in vitro Cultivation of the pathogens of Tropical Diseases. Tropical Diseases Research Series 3, Schwabe and Co. A G. Basel, pp. 251-272; Lemesre J L, Darcy F, Kweider M, Capron A, Santoro F, 1988. Requirements of defined cultivation conditions for standard growth of *Leishmonia* promastigotes in vitro. *Acta Trop* 45: 99-108; Ozbilgin A, Ozbel Y, Alkan M Z, Atambay, M, Ozcel M A, 1995. Cultivation of *Leishmonia* sp. in nutrient broth. *J Egypt Soc Parasitoi* 25: 437-41). Several serum-enriched tissue culture media; initially formulated for mammalian cells cultivation (viz. Eagle's minimum essential medium, TC-199 and Dulbecco's medium, Berens R. L, Brun R and Krassner S M, 1976. A simple monophasic medium for axenic culture of hemoflagellates. J. Parasitol. 62:360-365; Enders B, Brauns F and Zwisler O, 1977 Biochemical and technical consideration regarding the mass production of certain parasitic protozoa. Bull. W. H. O. 55: 393-402.; Childs G E, Foster K A and Mc Roberts M J, 1978. Insect cell culture media viz. Schneider's, Grace's and Mitsuhashi's medium, have now also been used successfully to cultivate several old and new world *Leishmanio* species. Reports suggested that supplemented insect cell culture media gave higher yields for wider range of *Leishmanio* spp. (Hendricks L D and Childs G E, 1980. Present knowledge of the in vitro cultivation of *Leishmanio*. The in vitro Cultivation of the pathogens of Tropical Diseases. Tropical Diseases Research Series 3, Schwabe and Co. A G. Basel, pp. 251-272) and Mitsuhashi's medium with 20% FCS supported a particularly different stock of *L. b. Braziliensis* (Walton B. C, Shaw j j and Lainson R, 1977. Observations on the in vitro cultivation of *Leishmania braziliensis* J. Parasitol. 63:1118-1119. Hendricks L D and Childs G E, 1980. Present knowledge of the in vitro cultivation of *Leishmanio*. The in vitro Cultivation of the pathogens of Tropical Diseases. Tropical Diseases Research Series 3, Schwabe and Co. A G. Basel, pp. 251-272).

Rabbit's blood is the most common and suitable additive of basal media.

However, the quarantine free animals through antibiotics-free diet to get the highest quality of rabbits' blood regularly/routinely for continuous supply of pooled rabbits' blood (to minimized the chance of anti-leishmanial effect, if present in any rabbit blood) for proper performance of the prepared culture medium is also a recurring expenditure resulting high cost of blood-based medium. The collection of blood from heart in sterile form from rabbits (Evans D A, 1986. An inexpensive easily available replacement for foetal calf serum in media for the in vitro cultivation of *Leishmanio* spp. *Z Parasitenkd* 72: 567-572) is also very expensive.

Though, FCS is an excellent supplement and replacement of blood in cell culture media that provides lots of defined and undefined essential components, yet, not acceptable because of killing the animals to provide serum. Moreover, FCS is highly expensive (high-quality FCS can cost up to $1000 per liter) and its reliable supply is difficult especially in developing countries (Chang K P and Hendricks L D, 1985. Laboratory cultivation and maintenance of *Leishmanio*: Chang, K. P. and Bray, R. S. (eds) Human Parasitic Diseases, Leishmaniasis. Amsterdam-New York-Oxford; Elsevier Science Publishers, 213-247; Newman C. 2003. Serum-free cell culture—the ethical, scientific and economic choice. Biomed. Scientist: 941-942). Serum can also harbour hazardous contaminants such as viruses, bacteria, prions, and mycoplasma (Newman C. 2003. Serum-free cell culture-the ethical, scientific and economic choice. Biomed. Scientist: 941-942). Above all, the increasing concerns about animal suffering inflicted during collection add an ethical imperative to move away from the use of serum wherever possible.

Various researches have been conducted to replace FBS with bovine serum albumin or a mixture of purine bases, vitamins, large concentrations of certain amino acids, hormones, hemin, hemoglobulin and, more recently, even human and animal urine (Ali S A, Iqbal J, Ahmed B and Masoom M, 1998. A semi-synthetic fetal calf serum-free medium for in vitro cultivation of *Leishmania* promastigotes. Am. J. Trop. Med. Hyg. 59: 163-165; Armstrong T C and Patterson J I, 1994. Cultivation of *Leishmania braziliensis* in an economical-serum-free medium containing human urine. J. Parasltol. 80 (6):1030-1032; Chaudhary G, Ghoshal K, Pal S and Banerjee A B, 1986a. A new medium for large-scale production of *Leishmania donovani* promastigotes for biochemical studies. Indian J. Med. Res. 84:457-460; Merlen T, Sereno D, Brajon N, Rostand F and Lemesre J L, 1999. *Leishmania* spp: completely defined medium without serum and macromolecules (CDM/LP) for the continuous in-vitro cultivation of infective promastigotes forms. Am. J. Trop. Med. Hyg. 60: 41-50; Pal J K and Purandare M J, 2001. Dose-dependent differential effect of hemin on protein synthesis and cell proliferation in *Leishmania donovani* promastigotes cultured in vitro. J. Biosci. 26: 225-231; Shamsuzzaman S M, Furuya M, Korenaga M, Imamura K and Hashiguchi Y, 1999. Use of urine samples from healthy humans, nephritis patients or other animals as an alternative to foetal calf serum the culture of *Leishmania* (*L.*) *donovani* in vitro. Ann. Trop. Med. Parasitol. 93 (6): 613-620). These media lacks whole serum as an ingredient, but it may not be entirely free of serum/blood/animal-derived products. These media may have defined quantities of purified obligatory growth factors of animal origin such as hemin/hemoglobin, serum albumin and other organics like peptone/extract/infusion of meat, liver, brain, heart including milk of animal origin to enrich the semi-defined medium. The chances of contamination either through animal-derived peptone/extract/infusion, or through hydrolyzing enzymes, if store in BSA, are also there. Being un-economical and un-ethical, involving complex procedures and laborious preparation, the animal product based culture media containing FCS/blood/blood products are still used due to the lack of proper alternatives/due to significant impediments in prior art. To overcome the potential problems of the use of serum/fresh blood, a need exists for products originating from plant sources that can support multiplication of *Leishmania* promastigotes.

OBJECTS OF THE INVENTION

It is therefore an object of this invention to propose a culture medium for Leishmania which uses plant derived natural components.

It is a further object of this invention to propose a culture medium for Leishmania, which uses easily available materials and is easy to prepare.

Another object of this invention is to propose a culture medium for Leishmania, which has sufficient storage durability.

Yet another object of this invention is to propose a culture medium for Leishmania, which is cost-effective.

A further object of this invention is to propose a culture medium for Leishmania, which is user-friendly and eco-friendly.

A still further object of this invention is to propose a culture medium for Leishmania, which is free from the risks involved with the use of animal products.

These and other objects and advantages of the invention will be apparent from the ensuing description.

DESCRIPTION OF THE INVENTION

Thus according to this invention is provided a plant extract based culture medium useful for growth of Leishmania promastigotes.

In accordance with this invention, is provided a plant based culture medium for in-vitro culture of Leishmania promastigotes, a parasitic haemoflagellate. The culture medium and medium supplement of plant's extract is a substitute for FCS/blood and other enrichment products of animal origin in basal medium, and is serum-free as well as totally product free.

In present invention, the best approach to culture Leishmania parasites mainly based on nutrition requirements considering the facts that apart from blood, adult female sand flies also take "plant diet".

After infective bites, since the developmental cycle of Leishmania promastigotes in sand fly is permanently restricted to alimentary canal, they exposed to the ingested tissues/sap of the various plants upon which the sand flies feed. Hence, the different plants' food composition will not only affect the sand flies, but there is probability that a considerable number of plants' food of local flora must play a crucial role in survival/propagation of Leishmania parasites present in the gut of naturally infected sand fly to continue/increase the potential of Leishmania transmission by bite.

Leishmania promastigotes require hemin as obligatory growth factor as they lack the enzymes i.e. aminolevulinate dehydratase and porphobilinogen deaminase which facilitate tetrapyrrole synthesis (Salzman T A, Stella Ana M., Xifra E A W de, Battle A M del C, Docampo R and Stoppani A O M, 1982. Porphyrin biosynthesis in parasitic hemoflagellates: functional and defective enzymes in *Trypanosoma cruzi*. Comp. Biochem. Physiol. 72B: 663-667).

It is also important that heme should be provided in optimum concentration. Studies revealed that normal protein synthesis and proliferation of promastigotes occurred at optimum concentration (10 μM) of hemin but its inhibition at higher concentration (50 μM) (Pal J K and Purandare M J, 2001).

Another obligatory nutritional requirement of *Leishmania* promastigotes is purine, as they are unable to synthesize purine de novo glycine, serine and formate, and require an exogenous source of purine for their active growth.

In addition, most of the parasitic protozoa including *Leishmania* require water-soluble vitamins for their better growth.

Further, since all plants even of same species do not show similar response owing to differ in their biochemical and physiological constitution due to climatic, edaphic and other factors and hence, in present invention, the potentiality of different plant's extract for cultivation of *Leishmania* promastigotes have been explored which was not known so far. In present invention, it has been found that plant's extract of a considerable number of plants of local flora supported proliferation of *Leishmania* promastigotes in long-term continuous successive sub-passaging. The invention provides novel culture media comprising plant-derived natural additive as essential growth factors for culturing promastigotes. No document is available in literature related to use of plant's extract as supplement/additive in culture media and for different related applications of promastigotes. The sue of plants' extract is an extremely economical alternative as medium additive, which can be prepared in bench-scale or in bulk from non-exhaustable, easily available nautra resources. Hence, in the field of culture media preparation, an attractive goal is achieved for hemoflagellate cultivation employing plant's extract as a medium supplement in medium having peptone and plant origin.

The plants used in the present invention are selected from the following:

| Plant Code | Botanical Name | Family |
|---|---|---|
| 5 | *Citrus maxima* | Rutaceae |
| 16 | *Thevetia peruviana* | Apocynaceae |
| 26 | *Croton bonplandianum* | Euphorbiaceae |
| 29 | *Benincasa hispida* | Cucurbitaceae |
| 15 | *Dolichos lablab* | Papilionaceae |
| 23 | *Calotropis procera* | Asclepiadaceae |
| 27 | *Colocasia esculenta* | Araceae |
| 28 | *Amorphophallus paeoniifolius* | Araceae |
| 24 | *Coccinia cordifolia* | Cucurbitaceae |
| 13 | *Amaranthus dubius* | Amaranthacesae |
| 42 | *Citrus aurantifelia* | Rutaceae |
| 41 | *Cucurbita pepo* | Cucurbitaceae |
| 1 | *Sesbania sesban* | Papilionaceae |
| 2 | *Solanum melongena* | Solanaceae |
| 44 | *Abutilon indicum* | Malvaceae |
| 48 | *Trianthema portulacastrum* | Aizoaceae |
| 43 | *Basella alba* | Basellaceae |

A novel (serum-free as well as totally animal product free) culture medium has been developed for in-vitro culture of *Leishmania* promastigotes—a parasitic hemoflagellate of human interest.

Promastigotes can propagate in claimed medium during long-term continuous successive sub-passaging.

In one embodiment, the culture medium comprise inorganic salts e.g. sodium chloride, potassium chloride, potassium dihydrogen phosphate, calcium chloride, and organic mixture e.g. glucose, yeast extract and peptone of plant source.

The plants' extract serve as an additive to provide the obligatory growth factor(s) for *Leishmania* promastigotes and their multiplication in-vitro in continuous manner.

Extract of various plants that exhibited propagative property, belongs to different families and possess different characteristics, have provided more choice in screening of plants to get (raw material) plants' extract easily and economically in different seasons and places, and for better acceptability and performance.

Culture medium as well as few plants' extract retained their capability to promote propagation even after autoclaving.

Culture medium (having 1% agar) supplemented with plant's extract is also capable and sensitive to promote cell growth from single cell to negate clonal populations, especially if maintained in animal product free medium.

Promastigotes (old/new isolates) can proliferate adequately in this nutritionally changed growth environment without need of sequential/special regimens for adaptation, prior to efficient long-term serial culture.

Promastigotes continuously sub-passaged in this medium when inoculated in susceptible animal; parasites recovered from spleen suggested retention of infectivity of promastigotes.

The complete medium can act as a serum/animal product free glycerol cryo-medium for preserving the culture from contamination with animal originated pathogens, which may incurred through use of animal product such as FCS/serum/infusion/extract/peptone etc.

Plants' extract either kept at least 3 years at −20° C. or 1 year at 4° C. or 6 months at room temperature, or even complete medium kept at 4° C. for at least 6 months exhibited luxuriant growth. Hence, the storage durability is quite enough for convenient utility.

The mass production of medium supplement as well as its vacuum dried product can be achieved in industry at a low cost.

The culture system is user-friendly, eco-friendly and in compliance with regulations, to meet the ever-increasing needs of promastigotes as well as for variety of related applications.

In the following description, a number of terms are used conventionally in the field of cell culture media. In order to provide a clear and consistent understanding of the specification and claims and the scope to be given, the following definitions are provided.

The term "*leishmanial*" refers to a genus responsible for the disease leishmaniasis.

"Leishmaniasis" is a disease caused by protozoan parasites that belong to the genus *Leishmania* and is transmitted by the bite of certain species of sand fly (subfamily Phlebotominae).

"Promastigotes" is the flagellate stage of a trypanosomatid protozoan, as that of any of the *Leishmania* parasites.

"Amastigotes" is a non-flagellated phase in the life cycle of trypanospme protozoans.

"Hemoflagellate" refers to a flagellate protozoan, such as a trypanosome, that is parasitic in the blood.

The term "cells" refers to individual cells as a whole/complete organisms or promastigotes of *Leishmania* spp.

"Proliferate" refers to the property of one cell dividing into two essentially identical cells or a population of cells increasing in number (e.g., to reproduce).

"Propagation" refers to growing (e.g., reproducing via cell proliferation) cells outside of tissue or the body, for example, in a sterile container such as a plastic/glass cell culture dish or flask.

"Cell culture" or "culture" refers to the maintenance/cultivation, growth, proliferation/propagation and/or differentiation of cells in an artificial in vitro environment.

"Cultivate" refers to the sustaining, propagating (growing) and/or differentiating of cells outside of tissue or the body.

The term "cultivation" refers to the maintenance of cells in-vitro under conditions favoring growth, differentiation or continued viability, in an active or quiescent state of the cells. "Cultivation" may be used interchangeably with "cell culture" or its probable synonyms such as sub-culture or sub-passage. "Cultivation" may utilize a culture medium as a source of nutrients and/or other factors helpful to propagate and/or sustain the cells.

"Capable of supporting the cultivation" refers to a condition that allows the survival and proliferation and/or differentiation, of isolated cells in culture.

"Passage"/"sub passage"/"sub culture" refers to the transfer of a certain portion of the cells from one culture vessel to another. It is understood that any time cells are transferred from one vessel to another vials having fresh complete medium, dilution of cells will occur.

"Passage number"/"sub passage number" refers to the number of times the cells in the culture have been subcultured or passaged.

"Serial passage" refers to the act of diluting and subdividing cells into multiple vessels when the cells have proliferated to a desired extent. As cells are passaged from the primary culture vessel into a subsequent set of vessels, the subsequent cultures may be referred to herein "first passage" etc.

"Long-term cultivation" refers to the cultivation of cells for long periods of time (months and/or years).

"Isolate" or "isolating" refers to separating and collecting cells from tissue or the body (ex-vivo) in culture medium.

"Primary culture" refers to cells, tissue and/or culture where the isolated cells are placed in a first culture vessel with culture medium. The cells, tissue and/or culture may be sustained and/or may proliferate, however, as long as the cells, tissue and/or culture remain in the first vessel the cells, tissue and culture are referred to as the primary culture.

The term "ingredient" refers to any chemically defined or semi defined (in their composition) material, whether of chemical or biological origin that can be used in cell culture media to maintain and/or promote the growth and/or proliferation of cells.

The terms "component", "nutrient" and "ingredient" can be used interchangeably and are all meant to refer to such compounds.

The "Infusion" is the outcome of material with desired chemical compounds. The ingredients, when admixed together in solution, form a "basal medium".

The cell culture media/basal medium/medium supplement of the present invention are aqueous-based and comprise a number of ingredients in a solution of deionized distilled water to form a "basal medium". Basal medium developed by inventors has also been used in present culture system.

Basal salt's solution of this invention is enriched with the common nutrients that comprise extracts of yeast cells (hereinafter "yeast extract"), peptone/infusion/extract of plant or animal origin and glucose to cultivate cells ex-vivo. This basal medium has been supplemented additionally with certain plant's extract.

The phrases "cell culture medium" or "culture medium" (plural "media" in each case) and "medium formulation" refer to a nutritive solution for cultivating cells and may be used interchangeably. Cell culture media provide the nutrients necessary to maintain and grow cells in a controlled, artificial and in-vitro environment. Cells cultivated in culture media metabolize available nutrients.

"Medium supplement" refers to nutritive compositions that help in maintenance/growth/proliferation of cell.

"Complete medium" refers to combining or mixing or admixing of supplement(s) in a cell culture medium formulation. At least one plant's extract is added to the basal medium to formulate the "complete culture media" of the present invention.

"Chemically semi defined medium" refers to a nutritive solution for culturing cells in which each component is not completely specifiable.

"Serum-free" medium means a medium that excludes serum of any type (e.g., fetal bovine serum, new born calf serum, horse serum, goat serum, etc.)

"Animal Product-free" medium means a medium that excludes any animal product such as serum, blood, hemin, hemoglobin, albumin, chicken embryo extract, peptone or extract or infusion of lean meat, brain, heart, liver, etc.

The term "culture vial/vessel" refers to a glass, plastic, or metal container that can provide an aseptic environment for culturing cells.

The term "plant's extract" refers to a composition (comprising a concentrated preparation of the component of a substance,) that may be formed by treatment of the substance/raw materials mechanically (e.g., by blending, grinding, pressure treating) in water and that have not been treated with heat or additional chemicals or bio-chemicals. This particular product is considered as a concentrated preparation of the component of the plant's extract. It is a "non-hydrolyzed" product/extract, though may contain a minor amount of hydrolyzed proteins due to hydrolysis by endogenous enzymes.

The term "enzymatic digest" refers to a composition comprising a specialized type of extract, namely one prepared by treating the substance to be extracted (e.g., plant components or yeast cells) with at least one enzyme capable of breaking down the components or the substance into simpler forms.

In this context, and for purpose of the present invention, the term "hydrolysate" may be used interchangeably with the term "enzymatic digest".

The term "non-animal derived", "non-animal ingredient" or "derived from non-animal sources" refer to the origin of the compound of interest. Here, such non-animal source may include preparation or extraction of materials of interest from members of plant kingdom e.g. plants and yeast cells.

"Plating" refers to spreading of cells on surface of solid medium.

"Clone" refers to a population of cells derived from a single cell by mitoses.

"Cryopreservation" refers to storage of cells in vapour/liquid Nitrogen.

"Infectivity" refers to establishment of infection in susceptible animals after in-vitro sub-passaging of organisms.

Materials and Methods

Selection of Plants:

The local herb and shrub plants (cultivated or wild, height <6", some of which having leaves at the soil level and stems not vertically erect) belonging to different families having different characteristics preferably provide food/good shelter to sand fly in different seasons and prevailing in the area of endemic villages of Bihar were selected randomly after site visit for the experiments.

Plants selection was based on the speculation that herbs and shrubs may provide suitable habitat for sand flies and probably give better chance of feeding in different seasons. Some tree like plants (shrubs) were also selected for preparation of plants' extract because these were common and branched with leaves at lower level (<6 ft) that may provide the same opportunity to vector. Plants were identified and coded.

Preparation of Plants' Extract:

The healthy plants free from insecticides/pesticides/fertilizers were collected in humidified poly bags from different places in different seasons during day time and brought to the laboratory immediately.

Plant's extract preparation was started within 2-3 hours after collection using stainless steel, glass, porcelain/china clay or plastic made equipments taking care to avoid product contamination with other components.

The plant's extract preparation procedure is as follows:

Soft leaves of each plant were washed thoroughly under running tap water until dirt and epiphytes present on its surface removed and finally washed thrice with doubled distilled water to remove tap water's traces.

Plants' leaves were blotted dried at room temperature, cut into small pieces (if required) and added with chilled double distilled water in 1:1 (w/v). The material was crushed using domestic applicant such as electric operated domestic mixture-grinder, mortar-pestles at low and/or moderate speed for 1-2 minutes avoiding generation of heat, and repeated for 6-7 times after cooling. The homogenate was strained through distilled water-washed muslin cloth to get a semi-clarified extract and allowed for freezing (at −20° C.) and thawing (at room temp.) for 2-3 times that facilitate breakdown as well as formation and removal of cold-insoluble material from non-hydrolyzed plant's extract. The homogenate was centrifuged at 4000-5000 rpm for 20-30 minutes and supernatant was filtered through Whatman filter paper no. -1/Whatman-40 filter paper. The filtrate was again centrifuged at 4000-5000 rpm for 20-30 minutes. Cold-insoluble material need not be removed from the solutions but may be removed for e.g., cosmetic reasons. After measuring the volume, antibiotic (Gentamycin-100 µg/ml) was added. Supernatant/filtrate was sterilized by Millipore filter (size-0.22 µm), aliquoted into sterile vials and frozen at −20° C. or at desired temperatures for different durations for future use, if other wise not stated.

Parasites:

L donovani promastigotes (KA/PKDL isolates) were isolated in biphasic medium (Brain heart infusion agar medium supplemented with 30% rabbit blood and having Locke's solution as overlay) from clinical materials of an Indian KA patients who was treated and cured with anti-leishmanial therapy.

Different species of Leishmania promastigotes such as L. tropica, L infantum and L. major were procured from other research organizations.

These promastigotes were maintained in-vitro by weekly sub-passaging in the biphasic medium having 10% rabbit blood or mono phasic medium having 10% heat inactivated FCS.

Same isolates were used in different experiments if otherwise not stated.

Culture Media:

For initial screening of plant's extract, sub-passaging was done in our innovative medium i.e. LGPY (Locke's salt solution supplemented with glucose, peptone (animal or plant origin) and yeast extract) to see the long-term propagative effects. After observing adequate propagation at least up to $20^{th}$ sub-passage, RPMI (RPMI-1640 with glutamine, 25 mM HEPES Buffer and sodium bicarbonate, pH-7.4) and SIM (Schneider's insect medium, pH-7.2) were compared with LGPY to see the suitability of extract for long term continuous successive sub-passaging of promastigotes. Antibiotic (Gentamycin-100 µg/ml) was used in culture medium.

Culture media were supplemented with 20% (v/v) of plant's extract, if other wise not stated. The same media with heat inactivated FCS (10%, v/v) were taken as positive control and plain medium was taken as negative control.

LGPY medium with heat inactivated FCS (10%, v/v) or BHI agar with 10% rabbit blood having Locke's solution as overlay was used to confirm the rejuvenation/survival of promastigotes. Same batch of FCS was used throughout the experiments.

Culture and Sub-Passages Conditions:

Before inoculation in experimental media, the promastigotes were sub-passaged at least 3 times in the same medium supplemented with FCS (10%, v/v) to recognize the basal media. Promastigotes of log phase culture were harvested and washed 3 times with sterile same plain medium at 2500 rpm for 20 minutes at 4° C. to remove traces of FCS/blood/hemin/hemoglobin in inoculum. The pallet was re-suspended in same cold medium and inoculated to get final concentration of $1 \times 10^5$ cells/ml in 5 ml screw caped glass culture vials having 990 μl of same culture medium supplemented with 5, 10 and 20% plants' extract (in experimental group), 10% FCS (in positive control) and plain culture medium in negative control). Two culture vials in each group were inoculated and were incubated at 24±1° C.

After inoculation of 5-7$^{th}$ day, wet smear of each culture vial was examined microscopically to see the effect of plants' extract on killing and survival of promastigotes in experimental as well as in both controls. Promastigotes viability was assessed in terms of their cell growth, flagellar motility and morphological changes (Habtemariam S, 2003. Cytotoxic and cytostatic activity of erlangerins from *Commiphora erlongeriono*. Toxicon. 41: 723-727), if promastigotes were active in sub-cultured vials, 10 μl from each culture vial was transferred into 2 corresponding fresh culture vials having same amount of medium. If motile promastigotes were not found even then successive sub-passaging was done further in corresponding culture medium till negative results obtained in following processes.

After inoculation, the rest suspension was centrifuged at 2000 rpm for 20 minutes to remove maximum effect of plants' extract. The pallet was dissolved in 50 μl LGPY without 10% FCS. A wet smear of this was examined microscopically for motile/sluggish promastigotes. If live promastigotes were found after centrifugation, subculture in LGPY having 10% FCS was not done, but If not, the rest suspension was inoculated in approximately 1 ml of LGPY medium with 10% FCS or Brain Heart Infusion Agar medium having 30% pooled defibrinated rabbit blood having Locke's solution as overlay, incubated at 24±1° C. and wet smears of it was examined at every 2-3 days up to 2 weeks for the presence of live promastigotes.

If all the promastigotes were found non-motile/degenerated during microscopic examination, it was thought to be negative at particular sub-passage, Again the above procedure was followed.

These steps helped to confirm the killing/lethal effect if parasites were not rejuvenated and those viable promastigotes, which had escaped observation during our microscopic examination. If the sub-culture failed to show any motile one, it was considered as ill effect of that plants' extract in particular medium at particular sub-passage.

Each experiment was done in duplicate vials.

In sub-passaging studies, growth density of promastigotes was determined microscopically in per high-power field (HPF) taking equal amount of cell suspension overlayed with equal sized cover-slip.

The invention will now be explained in greater details with the help of the following non-limiting examples:

Formulation of Basal LGPY Culture Media

The specific combinations of the ingredients, their concentration in the basal media are shown in table—1.

TABLE 1

The LGPY base medium
The LGPY base medium comprises inorganic salts of Locke's salts type and organic mixture.

| Inorganic mixture, i.e. | |
| --- | --- |
| Sodium Chloride | 8 g/l |
| Potassium Chloride | 200 mg/l |
| Potassium dihydrogen phosphate | 300 mg/l |
| Calcium chloride | 200 mg/l |
| Organic mixture, i.e. | |
| Glucose | 5 g/l |
| Yeast extract | 5 g/l |
| Peptone/hydrolysate and Plant extract | 10 g/l |

Details of peptone/fusion of animal or plant origin are as bellow.

In one embodiment, Peptone of animal origin (i.e. HIMEDIA, RM 001/RM 015/CR001).

In another embodiment, Soya Peptone (end product of enzymic, digestion of soyabean meal by papin—a plant origin based enzyme, HIMEDIA RM 007).

In another embodiment, HiVeg™ Peptone (an enzymic hydrolysate of vegetable protein, HIMEDIA RM 001V).

In another embodiment, HiVeg™ Infusion Power (obtained from vegetable proteins under controlled conditions, HIMEDIA RM 188V).

In another embodiment, HiVeg™ Hydrolysate (prepared under controlled condition by extracting vegetable proteins, HIMEDIA RM 023V)

All the ingredients were dissolved in 1000 ml double distilled water at pH 7.2-7.4 (pH was adjusted using NaOH). The solution was sterilized by 0.22 μm Milli pore filter.

For sterilization by autoclaving, some of the ingredients were dissolved separately as below and mixed after autoclaving to form a complete base medium.

The ingredients were taken in four flasks.

Flask—1 has NaCl, KCl, KH$_2$PO$_4$ and Peptone/Infusion, which dissolved in 700 ml distilled water and pH (7.4-7.5) was adjusted with NaOH.

Flask—2 has CaCl$_2$ which dissolved in 100 ml distilled water.

Flask—3 has Glucose which dissolved in 100 ml distilled water.

Flask—4 has Yeast extract which dissolved in 100 ml distilled water. After autoclaving, all solutions of three flasks mixed together in laminar airflow underneath the flame and antibiotic (Gentamycin-100 μg/ml) was added:

Above basal medium was supplemented with aqueous plant's extract (about 5-20%) as an obligatory additive like FCS/blood which is an inventive step.

EXAMPLE-2

2A. Effect of Plants' Extract in Continuous Successive Sub-Passaging of Promastigotes in FCS/Serum/Blood/Blood Products Free Medium i.e. LGPY Having Peptone of Animal Origin The hypothesis, that a considerable number of plant originated non-hydrolyzed product herein plants' extract might be helpful in propagation of promastigotes in long term continuous successive sub-culture, is verified through primary screening of plants' extract in FCS/serum/blood products free medium (if any). The plants have been selected and the inventors used 10% and 20% of plants' extract for approximation to optimum concentration for optimum best growth. Various mammalian culture media such as RPMI 16P9, medium 858 and L-15, all supplemented with 10% FCS, did not support the growth of *L donovani* for more than 2-3 subcultures, but in medium 199 with 10% FCS *L donavani* promastigotes was reported to be sub-cultured for 2-3 sub-passages (Berens R L, Brun R and Krassner S M. 1976. A simple monophasic medium for axenic culture of hemoflagellates. J. Parasitol. 62: 360-365) and *Lb. panamensis* (Hendricks L D, Wood D E and Hajduk M E. 1978. Hemoflagellates: Commercially available liquid media for rapid cultivation. Parasitology, 76: 309-316) for 17 weeks in the same medium with 30% FCS. Thus, a considerable number of sequential subcultures (usually at least 10) are required to establish a formulation as "growth medium" rather than merely a "holding" or "washing" medium.

Before inoculation in experimental medium, the isolate was processed as described previously in the heading culture and sub-passages conditions.

Plants' extract beneficial as a culture supplement in LGPY medium (possessed long-term proliferation promoting activity >15 sub-passages/=positive control) are disclosed in table—2, but may not be limited to these specific plants only.

Some plant's extract that possessed efficacy <=negative control or 15 sub-passages as a cell culture supplement in LGPY medium for promastigotes are also disclosed in table—2.

TABLE 2

Effects of Plants' extract on promastigotes based on number of successive sub passages

| Effects of plant's extract On promastigotes (compared to control) | Description of effect/ Survival in No. of sub-passages | Plant code no./ Total No. |
|---|---|---|
| Lethal/Harmful | Non-motile or deformed cells cells sustainment < negative Control (i.e. 0-4 sub-passages) | 7, 14, 19, 20, 21, 25, 32, 33, 34, 36 45, 46, 49/13 |
| Short-term survival/ Propagation/ sustentacular | Cells sustainment >= negative control/<= 15 sub-passages | 3, 4, 6, 8, 9, 10, 11, 12, 17, 18, 22, 35, 37, 38, 39/15 |
| Long-term survival/ Propagation/ sustentacular | Cells sustainment >= 15 sub-passages = positive control | 1, 2, 5, 13, 15, 16, 23, 24, 26, 27, 28, 29, 30, 31, 40, 41, 42, 43, 44, 47, 48/21 |
| Positive control | Cells sustainment >= 15 sub-passages | At least 55 |
| Negetive control | 5 | |

Some details and noticeable characteristics of plants' extract exhibited long-term proliferative effect are mentioned in table—3.

TABLE 3

Plants characteristics of which extract exhibited long term proliferative effect.

| Family | Plant Code | Plant Name | C/W | Age(A/P) | Habitat (M/X) |
|---|---|---|---|---|---|
| Acanthaceae | 49 | | W | A | M |
| Amaranthaceae | 13 | | C | A | M |
| Apocynaceae | 16 | | C/W | P | X |
| Asclepiadaceous | 23 | | W | P | X |
| Araceae | 27 | | C | A | X |
| | 28 | | C/W | A | M |
| Cucurbitaceae | 24 | | W | A | M |
| | 29 | | C | A | M |
| | 33 | | C | A | M |
| | 41 | | C | A | M |
| Euphorbiaceae | 26 | | W | A | — |
| Graminae | 34 | | W | A | M |
| Ipomeaceae | 35 | | W | A | M |
| | 36 | | W | A | M |
| Lamiaceae | 45 | | W | A | M + X |
| | 46 | | W | A | M |
| Mimoceae | 39 | | W | A | M |
| Malvaceae | 31 | | C | P | M |
| | 40 | | C | A | M |
| | 44 | | W | A | M + X |
| Papilionaceae | 1 | | C | A | M |
| | 15 | | C | A | M |
| Piperaceae | 30 | | C | P | M |
| Rutacea | 5 | | C | P | M |
| | 42 | | C | P | M |
| | 43 | | C | A | M |
| Solanaceae | 2 | | C | A | M |
| | 32 | | W | A | M |
| | 37 | | C | A | M |
| | 38 | | C | A | M |
| Umbellifereae | 47 | | W | A | M |
| | 48 | | W | A | M |

A/P—Annual/Perennial 1, M/X—Mesophytic/Xerophytic, C/W—Cultivated/Wild.

Surprisingly, supplementation of one plant's extract (10-20%) in LGPY medium exhibited successful proliferation of promastigotes at least up to 74 sub-passage and approximately ⅔ of tested plants' extract showed adequate proliferation at least up to 55 sub-passages.

Hence, this propagative property of plants' extract is evident in a considerable number of plants of different families/categories having different characteristics. Though, the propagative effect do not observed only in particular families as all members of the same family did not show similar response. Both, beneficial as well as harmful effect was observed in plant's extract of the same family, such as Cucurbitaceae (4 out of 6 plants' extract), Solanaceae (4 out of 8 plants' extract) and Malvaceae (3 out of 3 plants' extract) showed long-term proliferative effect.

Results showed that the nature of plants (i.e. mesophytic, xerophytic) did not show any correlation with growth promoting ability of plants' extract. The selection of plants to get plants' extract as a product could be based upon factors such as, their availability in different seasons and places, easy cultivation in agricultural or bare land for mass production of plant's extract for commercialization as well as bench scale production and collection of raw material in sufficient amounts and its processing under controlled conditions.

Some plants with soft, easily harvestable leaves (e.g. 1, 2, 13, 15, 16, 27, 28, 29, 30, 40, 41, 43, 48) can be cultivated easily to get adequate amount of raw material.

Some plants are cultivated for use as a leafy vegetable (e.g. 13, 27, 41, 43, 48) or to get their fruits (e.g. 5, 42) or fruits as a vegetable (e.g. 2, 15, 29, 40, 41) or corns for vegetables (e.g. 27, 28), and available in every seasons and place.

Some of the plants are perennial (t.g. 5, 16, 23, 42) or ornamental (e.g. 16, 31) and can serve whole year by providing abundant leaves.

The wild plants (e.g. 23, 24, 26, 44, 47) grow abundantly on uncultivated land around the peridomestic areas or in rural/sub urban farm, may also be available at free of cost.

During experiments of serial propagation of promastigotes, the inventors discovered the non-hydrolysed plant derived extract supplement as a good substitute of FCS/blood/its products in the medium which is cheap and readily available. This indicated the possibility of presence of some yet uncharacterized growth factor (s) in plants' extract that stimulate(s) proliferation of *L. donovoni* promastigotes. This ensures the presence of some active component(s) in plants' extract for replacement of animal's product additives i.e. FCS/serum/blood or its products.

Plant based natural biological fluid i.e. non hydrolysed plants' extract might be a good source of heme containing substances like cytochromes, catalases/peroxidases as well as for purine and Water-soluble vitamin B that may fulfil the requirement of obligatory growth factors as well as growth promoting factors. In negative control, promastigotes died just after few successive sub-passages if might not be supplied sufficient quantity of heme which is critical cofactor for many biological processes. In short and long-term propagative group, proliferation of promastigotes might be a result of combined effect of harmful as well as beneficial components (whatever it is) present in the same extract in variable concentration.

Plant's product, herein, plant s extract can be a good alternative for replacing FCS/serum/blood/blood-product in basal culture medium to support multiplication of promastigotes, which is an objective of present study and is achieved through discovery that plant's extract of a considerable number of plants of local flora has supporting effect in proliferation of *Leishmonia* promastigotes in long-term continuous successive sub-passaging.

In another embodiment, plants which raw leaves' extract ensured propagative effect in serial culture were selected to ensure whether extract of dried leaves will retain their obligatory growth factor(s) sufficient to replace FCS/blood or not. Aqueous extract from dried leaves of 3 plants' were prepared and dried. Then, medium was supplemented with dried extract at 3 different concentrations i.e. 5, 25 and 50 mg/ml (table 4).

TABLE 4

Confirmation of fertility properties of APF medium having 3 extracts from dried leaves of 3 plants at 3 different conc. Results are based on survival up to No. of SP.

| Solvents | Survival in SP No. D.W. | | |
|---|---|---|---|
| Conc. (mg/ml) PE Code | 5 | 25 | 50 |
| 5 | 2 | 2 | 1 |
| 15 | 3 | 2 | 1 |
| 16 | 3 | 5 | 3 |
| Negative Control | 4 (only plain medium) | | |
| Positive Control | 10 continued (medium with FCS) | | |

The results showed that obligatory growth factor lost during processing. Hence, our plants' extract preparation procedure to supplement medium for serial culture of *Leishmario* promastigote was a inventive step.

Use of extracts of aloe-vera plant leaves has already been suggested (PCT Application No. PCT/US99/09574). Unfortunately, test results demonstrate that aloe-vera lea powder extracts do not possess activity sufficient to replace bovine pituitary extract (BPE) as a supplement because the extract lacks BPE's proliferation-promoting activity for important cell types (US Pat. Appli. No. 20060094114).

LGPY medium supplemented will vacuum dried extract obtained from raw leaves has also exhibited long term continuous successive sub passasing.

2B. Effects of Plants' Extract in Continuous Successive Sub-Passaging Process of Promastigotes in Completely Animal Products Free Medium i.e. LGPY Medium to Ensure the Long Term Propagation A number of semi-defined media, enriched with a variety of organics (including peptone, beef infusion, tryptose, liver extract, brain heart infusion, yeast extract and, of course, fresh blood-chiefly pooled rabbit blood or FCS at concentrations ranged from 10-20%) have been used successfully to culture *Leishmania* promastigotes.

Taking lead from previous observations, to develop completely Animal Product Free culture medium for propagation of *Leishmania* promastigotes and their utility for different related applications, FCS/blood or its products including peptone of animal origin of our trial medium was replaced by 4 different commercially available peptone/hydrolysate or infusion of plant origin (as the composition depend upon source as well as processing, and small change in medium enrichment is also among the different factors that can have drastic effect on cell growth and propagation) to satisfy nutritional contributions, and were supplemented with 4 different plant's extract in 3 different concentrations (i.e. 20, 10 and 5%) to confirm the fertility properties of the culture medium for long-term continuous successive sub-passaging of promastigotes.

Adequate proliferation of promastigotes was exhibited at least 40 sub-passages in all media i.e. LGPY medium having peptone/infusion and extract of plant's origin (table—5). This confirmed the survival of promastigotes in continuous successive sub-passaging in completely APF medium. This reality was not known since starting from NNN. However, 3 trial media having different peptone of plant origin did not support long-term propagation of promastigotes, even after supplemented with 10% FCS.

TABLE 5

Confirmation of long-term propagation of promastigotes in APF medium having supplements of plant origin

| Peptone/infusion | Survival in Sp No. PE code (conc. 5-20%) | | | | Control | |
|---|---|---|---|---|---|---|
| from plant | 5 | 16 | 26 | 29 | +ve | −ve |
| P | 40 | 40 | 40 | 40 | 5 | 2 |
| SP | 40 | 40 | 40 | 40 | 4 | 3 |
| HI | 40 | 40 | 40 | 40 | 3 | 3 |
| Si | 40 | 40 | 40 | 40 | 40 | 4 |

SP—sub passage;
PE—plant's extract;
P, HI & Sp—different peptone;
Si—infusion

Ignoring the rate of proliferation, these sub-passage numbers are quite enough to confirm that the medium supplemented with only plants' products can be used for long-term propagation of *Leishmania* promastigotes. Thus, in this culture system (vegetarian culture medium), components of plant's origin can satisfy all nutritional requirements of promastigotes for their growth and reproduction as similar to FBS/blood or its products along with other enrichments of animal origin.

Thus, the present invention relates to methods for replacing all animal natural-products such as FCS/serum/blood, or animal-derived products such as hemin/hemoglobin/peptides or infusion or extract etc. from plant (non-hydrolysed natural-products) along with plant-derived products i.e. peptides or infusion or extract. Such plant nutrients may be substitute for any number of, animal-originated culture medium components or substituents, including but not limited to blood derived products in the culture media of the invention. Hence, a substantial useful progress has been achieved by this new technological approach, which is fast, efficient, simpler and cost-effective.

The promastigotes proliferated well in plant-based medium indicating that plant extract's could be a source of heme containing substances, as the components of basal medium did not have the iron source.

EXAMPLES-3

Microscopical Determination of Morphological Changes (Morphological Studies)

The morphological characteristics of the cultured promastigote form according to the invention were compared with the promastigote form cultured in conventional medium by light-optical microscopy because cells tend to be more sensitive and fragile when cultured in animal product-free medium.

During continuous successive sub-passaging in this medium, wet-smear and Giemsa stained smear of log phase promastigote culture was examined microscopically for presence of abnormal or atypical morphology. They retained their general morphological/cytological characteristics; indicated that plant extract as medium supplement is good for health and long-term propagation of promastigotes.

EXAMPLE-4

Comparison for Long-Term Propagative Effect in Different Media Supplemented with Different Plant's Extract:

To determine long term propagative effect of plants' extract in two commercially available media (mammalian cell culture medium and insect cell culture medium), plants' extract (20%, v/v) were supplemented with Schneider's Insect medium (SIM) and RPMI (RPMI-1640 with glutamine, 25 mM HEPES Buffer and Sodium bicarbonate) that have shown beneficial effect with LGPY medium in long-term sub-passaging of promastigotes.

Antibiotics (100 µ/ml, Gentamycin or 100 IU/ml Pencillin and 100 µg/ml Streptomycin) were used in medium. The propagative effect was compared with LGPY having same plants' extract at same concentration. The medium with heat inactivated FCS (10%, v/v) were taken for positive control and plain medium as negative control. Complete LGPY medium (FCS 10%, v/v) was used to confirm the rejuvenation/survival of promastigotes, which have escaped observation during our microscopic examination. Each experiment was done in duplicate.

Two commercially available media (RPMI-1640 and SIM) and LGPY were compared using 9 different plants' extract, all 9 plants' extracts showed long term propagation in LGPY, whilst only 6 and 3 plants' extract out of 9 extracts' in SIM and RPMI-1640 respectively favor the long term propagation at least up to 55 continuous successive sub-passages.

In present invention, 3 plants' extract favors the propagation at least up to 55 continuous successive sub-passages in all the three culture media.

Results demonstrated that the composition of the basal medium is essential to the ability of the disclosed non-hydrolyzed plant extract supplements to support the growth of, for example, *Leishmania* promastigotes.

*Leishmania* promastigotes are unable to synthesize purine (an essential growth factor) de novo from glysine, serine and formate and require an exogenous source of purine for their growth. There is no purine base in both commercially available media (i.e. RPMI-1640 and Schneider's insect medium), and plant's extract alone may not, be able to fulfill the purine requirement in these media. Hence, promastigotes died after certain subsequent sub-passaging with some plant's extract. Whereas, in LGPY, yeast extract and peptone are the good source of purine and thus supported the growth of promastigotes.

It has been reported that RPMI 1629, medium 858 and L-15 all supplemented with 10% FCS did not support the growth of *L. donovani* for more than 2-3 subcultures and could only be cultured for 2-3 subpassages in medium 199 with 10% FCS (Berens R L, Brun R and Krassner S M, 1976. A simple monophasic medium for axenic culture of hemoflagellates. J. Parasitol. 62: 360-365), while *L. 5. panamensis* (Hendricks L D, Wood D E and Hajduk M E, 1978. Hemoflagellates: Commercially available liquid media for rapid cultivation. Parasitology, 76:309-316) was sub cultured for 17 weeks in medium 199 with 30% FCS.

Hence, different basal media are not equally good to support proliferation with same/different plants' extract in this culture condition, and ingredients of basal medium itself can affect much. In this way, our formulation of basal medium is found ideal/better growth promoter in this culture condition.

The formulation according to the invention of basal medium is enriched with glucose, peptone and yeast extract. In fact, *Leishmania* promastigotes can grow in vitro without glucose, provided that amino acids such as proline and glutamate are present in culture medium But, even then glucose was added as it was found that D-glucose and non-esterified fatty acids stimulated promastigotes respiration and amastigotes transformation to promastigotes in vitro. Peptone and yeast extract contribute mainly for nitrogenous components such as amino acids, nucleic acid bases, vitamins.

TABLE: 6

Effect of different plant's extract (n = 13) on growth of promastigotes based on No. of successive SP in 3 different culture media.

| PE Code & control | Survival in No. of SP | | |
|---|---|---|---|
| | RPMI | SIM | LGPY |
| 27 | 4 | 3 | 55 |
| 2 | 4 | 4 | 55 |
| 5 | 55 | 5 | 55 |
| 13 | 5 | 55 | 55 |
| 16 & 26 | 6 | 55 | 55 |
| 15, 28, 29 (9/3) | 55 | 55 | 55 |
| Positive control | 55 | 55 | 55 |
| Negative control | 4 | 3 | 5 |
| | 9/4 | 9/6 | 9/9 |

PE—plants' extract,
SP—sub-passage

EXAMPLE-5

Determination of Temperature Stability at 121° C. for 20 Minutes:

Autoclaving is the most economical, convenient, safe and reliable sterilization method that increases the practical acceptability for medium preparation. Hence, to confirm the thermal stability of medium as well as plants' extract (found suitable in long-term maintenance of promastigotes in LGPY medium previously) were autoclaved at 121° C./15 lb for 20 minutes and supplemented (20% v/v) in the same medium after autoclaving followed by continuous successive sub passaging of promastigotes.

Interestingly, 2 (code—5 & 29, table—9) out of 21 exhibited adequate growth in long-term continuous successive sub-passaging of promastigotes in ca. 50 sub-passages in-vitro cultures.

This ensured the growth factor of at least certain plants' extracts as heat stable at 121° C. for 20 minutes, might be due to its intrinsic as well as extrinsic influences such as, presence of some other component in plants' extracts, retention at particular pH etc.

Hence, at least few plants' extracts can be used after sterilization by moist heat which are well-suited with respect to limited laboratory facilities and increase the practical utility and acceptability. The fulfills one of the objects of invention i.e. to provide an autoclavable medium supplement as well as basal medium to produce completely autoclavable medium for long-term propagation of promastigotes.

TABLE 7

Thermal stability (at 121° C. for 20 min) of plants' extract used for promoting growth of *Leishmania* promastigotes.

| PE Code & control no | Total no. of PE | Survival in SP. |
|---|---|---|
| 40 | 1 | 0 |
| 42 | 1 | 3 |
| 1, 2, 16, 24, 26-28, 31, 43, 44, 47 | 11 | 5 |
| 30 | 1 | 7 |
| 41 | 1 | 8 |
| 23, 48 | 2 | 10 |
| 15 | 1 | 13 |
| 13 | 1 | 20 |
| 5, 29 | 2 | 40 (21/2) |
| Positive control |  | 40 |
| Negative control |  | 5 |

PE—plants' extract,
SP—sub-passage

EXAMPLE-6

Evaluation of Growth:

During experiments, adequate number of promastigotes was observed in LGPY medium supplemented with various plants' extract in long term continuous successive sub passaging of promastigotes. It was not known whether propagation of parasites in plants' extract supplemented medium is quit enough/at par to FCS supplemented medium or not. Hence, it is worthwhile to illustrate the final density of particular cells in new medium for different studies.

To clear this fact, experiment was done in 15 ml culture vial. LGPY medium was supplemented with randomly selected extract (stored at −20° C. for 3 years) of 2 plants (perennial, 1 mesophytic & 1 xerophytic) in 3 different concentrations (i.e. 20%, 10% and 5%). LGPY medium with FCS (10%) was taken as control. These media were inoculated with $1\times10^5$ cells/ml. Total number of cells was counted at every 24 hrs.

Supplementation of LGPY medium with another plant extract (code—16) at 20% and 10% concentration, maximum growth crossed $1\times10^8$ cells/ml (i.e. approx. $1.3\times10^8$ cells/ml) on $7^{th}$ day. Hence, these concentrations are quite enough for mass/routine culture of promastogotes which can provide large number of parasites in a short period of time (i.e. $7^{th}$ days) at extremely low cost. At 5% concentration of plants' extract, the maximum growth crossed $1\times10^7$ cells/ml (i.e. $7.3\times10^7$ cells/ml) on $7^{th}$ days. This may be used for routine maintenance of promastigotes. Survival of promastigotes was observed at least 7 weeks.

Supplementation of LGPY medium with another plant extract (code—5) at 20% concentration, maximum growth crossed $1\times10^8$ cells/ml (i.e. $1.1\times10^8$ cells/ml). The cell density was only little less at 10% supplementation (i.e. approximately $9.2\times10^7$ cells/ml). Survival of promastigotes was observed at least 8 and 7 weeks, respectively. Hence, these concentrations are quite enough for mass/routine culture of promastigotes which can provide large number of parasites in a short period of time (i.e. $6^{th}$ days) at extremely low cost. At 5% concentration of plants' extract, cell concentration was $5.3\times10^7$ cells/ml on $8^{th}$ day. Survival of promastigotes was observed at least 2 weeks. Hence, culture at this concentration may be used for routine sub passasing of promastigotes.

Hence, it was found that number of parasites depends upon concentrations and types of plant's extract. Different phases of promastigotes in culture medium were also clear to work on different phases of promastigotes.

Supplementation of LGPY medium with FCS (10%) exhibited $3.76\times10^7$ cells/ml on $12^{th}$ day and survival of promastigotes was observed at least 7 weeks. Each experiment was done in duplicate.

EXAMPLE-7

Evaluation of Low Inoculum Size for Adequate Propagation of Promastigotes:

It is also advisable that thresh hold of the inoculum size of cell/low inoculum size of cell (here, $<1\times10^5$ promastigotes/ml) for propagation in the newly developed culture medium need to be determined.

To determine the low inoculum size of promastigotes for adequate propagation, LGPY medium having 10% concentration of one plants' extract (code—16) was inoculated with promastigotes at 3 different final concentration i.e. $1\times10^4$, $1\times10^3$ and $1\times10^2$ cells/ml. The total number of cells was counted on 3 successive day (i.e. $7^{th}$, $8^{th}$ and $9^{th}$ day) starting from $7^{th}$ day, because maximum growth was observed on. $7^{th}$ day with higher inoculum (i.e. $1\times10^5$ cells/ml).

When LGPY medium supplemented with plant-extract was inoculated with $1\times10^4$ cells/ml, total number of cells/ml was approximately $3.6\times10^7$ cells/ml on $9^{th}$ day. When inoculated with $1\times10^3$, total number of cells/ml was around $1.5\times10^7$ cells/ml on $9^{th}$ day. It was also observed that plant extracts support cultivation of parasite even at very low inoculums size ($1\times10^2$ parasites/ml). When inoculated with $1\times10^2$, total number of cells/ml was around $0.49\times10^7$ cells/ml on $9^{th}$ day. These promastigotes were very active.

Hence, LGPY medium with plant's extract is also quite sensitive to propagate promastigotes in adequate number and may be used in routine in vitro maintenance of different isolates.

EXAMPLE-8

Determination of Effect of Storage Conditions (Temperatures and Durations):

While developing a new medium, it is important that basal medium, medium additive and complete medium should have adequate storage durability.

Plants' extract, complete medium and basal medium were stored at different temperatures (i.e., −20° C., +4° C. and room temperature) for different period of time (i.e., 4 years, 1, year, 9 months and 6 months) to evaluate the growth at different time period.

The complete medium were inoculated with equal number of promastigotes (i.e., $1\times10^5$ cells/ml) to determine any noticeable/remarkable difference in density/population of promastigotes during continuous successive sub-passaging on 6-$7^{th}$ days at different time period. The number was evaluated microscopially by 40× objective taking equal amount (i.e., 15 µl) of cell suspension on microscopic slide covered with equal size (18×18 mm) of cover glass.

The stability studies of the medium, complete medium and plant's extract products at different storage temperatures and durations demonstrate that the storage stability of the frozen plants' supplement are quite sufficient (at least 4 years) from the date of manufacture providing extra benefit to use for long duration like FCS. It could be stored at +4° C. for 1 year and at least 6 months at room temperature. Promastigotes were capable of undergoing long-term cultivation.

Since the basal medium as well as complete medium stored at room temperature for a quite considerable period of time (at least 6 months) did not lost the growth promoting properties of the plant's extract saves valuable refrigeration space/reduced requirements for media storage and easy in transportation, if required.

TABLE 8

Effect of temperatures and durations on LGPY medium, plants' extract and LGPY medium with plants' extract. Effect of storage conditions (temp. & duration)

| Material (cells/ml) | RT | +4° C. | −20° C. | Growth |
|---|---|---|---|---|
| PE | 6 m | 12 m | 36 m | Luxuriant |
| LGPY | | 6 m | | Luxuriant |
| LGPY + PE | | 6 m | | Luxuriant |
| | | 9 m | | Poor |
| | | 12 m | | Nil |

PE—plant's extract,
m—month,
Luxuriant—>4.0 cells/HPF,
Poor—<10 cells/HPF

EXAMPLE-9

To Determine Adaptive Capability in New Growth Environment:

Some cells are very sensitive to physiochemical and nutritional changes and may take more than 8 consecutive passages for the adaptation (Hyq® CDM4NSO™). Sometimes special regimens are or may be required to adapt insect cells (CHO and BHK cells to protein-free express media of different origin) from serum containing to serum free SF-3/SF-4 media: direct and gradual replacement (weaning).

Primary isolation of promastigotes was done in plant's extract (Code No. 5, 16, 26 and 29) supplemented LGPY medium, and/or in blood based biphasic medium or FCS based monophasic medium. These isolates were continuously successively sub-passaged in corresponding medium as mentioned above.

Newly isolated or serially sub-passaged promastigotes from blood/serum based medium were also inoculated into plant's extract based medium to determine adaptive capability in nutritionally changed growth environment.

Promastigotes from blood/serum based medium when directly inoculated after three washing into the plants' extract based trial medium, grew very well to the new growth environment, which indicated that prior to culture, sequential adaptation of promastigotes to grow in serum-free media is not required.

TABLE 9

To determine adaptive capability in new growth environment

| Clinical material | Isolate No | Isolation medium | Sub-passaging medium | Growth |
|---|---|---|---|---|
| Splenic aspirate | 8,8118 | LGPY + PE | NNN, LGPY + FCS & LGPY + PE | Luxuriant |
| Skin biopsy | 247 | NNN | NNN, LGPY + FCS LGPY + PE | Luxuriant |

PE—plants' extract

EXAMPLE-10

Determination of Colony Formation of Promastigotes on Solid Medium:

For cell cloning, agar plating is a very appropriate technique as being sensitive and less laborious than competing methods. The colony formation ability of *Leishmania* spp. on solid medium are exploited for immunological (Handman E, Hocking R E, Mitchell G F and Spithill T W, 1983. Isolation and characterization of infective and non-infective clones of *Leishmania tropica*. Molecular and Biochemical Parasitology 7, 111-126), physiological (Simpson L, 1968. The *Leishmania* Leptomonad transformation of *Leishmania donovani*: Nutritional requirements, respiration changes and antigenic changes. J. Protozol. 15: 201-207; Wagner K P and Krassner S M 1976. *Leishmania tarentolae*: streptomycin and chloramphenicol resistance of promastigotes. Exp. Parasitol. 39: 222-233), genetic, drug sensitivity analysis (Pal S, Mandal A and Duttagupta S, 2001. Studies on Stibanate resistant *Leishmania donovani* isolates of Indian origin; Indian J. Exp. Biol. 39 249-254; Bhattacharyya A, Mukherjee M and Duttagupta S, 2002. Studies on Stibanate unresponsive isolates of *Leishmania donovani*. J. Biosci. 27: 503-508) and virulence etc. For this a few medium has been evaluated for their efficacy (Keppal A D and Janovy J Jr., 1980. Morphology of *Leishmania donovani* colonies grown on blood agar plates. J. Parasitol. 66: 849-851; Iovannisci D M and Ullman B, 1983) High efficiency plating method for *Leishmania* promastigotes in semi-defined or completely defined medium. J. Parasitol. 69: 633-636; Hill J O and Fahey J R, 1987. *Leishmania* spp; Agar plating as an alternative to limiting dilution and impression smears for the enumeration of viable parasites in tissue: 63: 108-111; Kar K, 1997. Folic acid the essential supplement to brain heart infusion broth for cultivation and cloning of *Leishmania donovani* promastigotes. Parasitology, 115: 231-235; Kar K, Mukerji K, Naskar K, Bhattacharya A and Gosh D K, 1990. *Leishmania donovani*: a chemically defined medium suitable for cultivation and cloning of promastigotes and transformation of amastigotes to promastigotes. J. Protozool. 37:

227-279). Growth as colonies on agar plates also offers some other important advantages such as, generation of large number, of clones and their easy quantification on a single plate, determination of relative growth rates by direct visualization of colony size, enumeration of viable parasites present in a tissue, transfer of clones en masse to solid support (e.g. nitrocellulose membrane) for rapid screening, determination of nutrient requirements of cells, measurement of growth affecting factors, toxicity testing etc. Hence, a colony formation efficacy in this novel medium was also determined.

To elucidate the colony formation from single cell on 1% agar base in LGPY medium supplemented with 3 different plants' extract (20% v/v), 2 Petri plates of each were inoculated with 3 cells/plate which was achieved by dilution of an original cell population down to 3 cells in 50 µl. For positive control, 10% freshly obtained defibrinated rabbit blood was mixed with LGPY medium having agar (1%). The promastigotes colonies were counted and were compared with controls. The material of each colony was scratched by sterile loop and suspended in plain medium. Wet smear was examined under microscope for viability of cells. Colonies diameters were measured.

Whitish-mucoid viable colonies of 3 to 4 mm size were observed on $10^{th}$ day in each plate. As it is a measure of the number of colonies originating from single cells; it is clear that this medium (could also pick up small inoculums to proliferate) is also very sensitive and useful for the selection of single-cell colonies and has supported high cell densities with good viability and high productivity levels without the use of animal-derived compounds. This formulation was tested with 3 different plant's extract and was shown to generate comparable results, in term of clonal survival and growth. Thus, the plant's extract supplemented medium supports *Leishmania* promastigotes clonal survival and growth comparable to 10% FBS supplemented basal medium.

On this basis, this invention claims that serum-free medium is comparable to serum-supplemented media. In order to address the regulatory needs, it is an object of the present invention to provide a culture medium for Animal Component—Free cloning that is capable of sustaining growth of *Leishmania* promastigotes at very low cell density conditions, and which is equivalent in cell cloning efficiency of media having serum.

TABLE 10

Evaluation of colony formation (on 1% agar-base in LGPY with 20% PE, inoculum 3 cells/plate)

| PE code (n = 3) | No. of colony on $10^{th}$ day | |
|---|---|---|
| | Plate I | Plate II |
| 5 | 2 | 3 |
| 16 | 3 | 2 |
| 26 | 4 | 2 |
| Positive control (LGPY + 10% FCS) | 2 | 3 |

EXAMPLE-11

Cryopreservation

Serum-particularly FBS—is used universally as a cryoprotective additive to enhance the long-term cryostability of cells. If cells are grown in serum free medium, it is advisable to cryopreserve the cells in serum free medium due to various reasons. The serum free freezing media such as Promo cell's Cryo-SF M formulation, Hyclone Hyq® CDM4NSO™ formulation (Hyq® CDM4Retino™; Hyq® SFM4CHO™; Hyq® CDM4NS™; Hyq® CDM4m Ab™; Hyq® ADCF-mAb™) have been developed to cryopreserved the cells. In a serum-free cell culture system, the cells are cryopreserved in a serum-free freezing medium.

Use of serum-free cryopreservation media for protozoan parasites like *Leishmania* promastigotes has received much less attention. Thus, the search for animal-source-free cryopreservation medium formulations has become an important focus for culturist for long-term storage of cell banks which is non-obvious.

After primary isolation, mass culture of the parasites were grown in LGPY medium having 10% four different plants' extract (n=4, Code No. 5, 16, 26 & 29). Mid-log-phase culture of promastiogotes was harvested by centrifugation for 20 minutes at 2500 rpm at 4° C. Number of promastigotes was adjusted to $2 \times 10^7$ cells/ml in both experimental (LGPY medium with 20-30% plant's extract) and control (LGPY medium with 20-30% FCS) group. Each group was supplemented with 16% Glycerol. Equal volume of cold cryopretective medium was added drop by drop in cold parasites' suspension. The vials were cooled slowly and kept in liquid nitrogen finally.

Cryopreserved promastigotes were examined after six months up to one and half year for their viability. Stabilities were thawed rapidly at 37° C. in water bath, further examined microsopically for their motility and sub-cultured aseptically into same kind of culture medium in which the cryopreserved promastigotes were grown before freezing. Sub culture was examined on $8^{th}$ days.

During wet smear examination, both motile and sluggish promastigotes exhibited luxurious growth on $8^{th}$ day in first and further sub-passages.

In freezing test, the cells viability, frozen in the experimental medium, was good and for 1.5 year the result was similar to those grown and frozen in conventional medium. Furthermore, time for re-establishing cell division on thawing is also similar to conventional medium. Cells cryopreserved in this showed good performance after thawing in successive culture. Henceforth, it may act as a serum-free glycerol cryo-medium/cell freezing glycerol medium—serum free giving no chance of contamination of the culture through serum in the freezing medium.

Protozoa require cryoprotective agent when refrigerated at low temperature. Meryman H T, 1971. Cryoprotective agents. Cryobiology 8:173-183). Glucose has been found as a natural cryoprotective agent to help counteract the osmotic shock and control changes in volume of tissue cells in *Rana sylvatica* (Devireddy R V, Barratt P R, Storey K B and Bischof, J C, 1999. Liver freezing response of the freeze-tolerant wood frog, *Rana sylvatica*, in the presence and absence of glucose. I. Experimental measurements. *Cryobiology* 38, 310-326) which is able to tolerate freezing temperatures as low as −6° C. to 8° C. and durations of freezing of 2 weeks or more with multiple freeze-thaw cycles. A combination of 10% DMSO and 8% (v/v) glucose has been used to preserve strains of Deuteromycetes (Dietz A and Currie S, 1996. Actinomycetes, in Maintaining Cultures for Biotechnology and Industry (Hunter-Cevera, J. C. and Belt, A., eds), Academic Press, Inc., San Diego, Calif., pp. 85-99).

Sucrose and trehalose (Beattie G M, Crowe J H, Lopez A D, Cirulli V, Ricordi C and Hayek A; 1997. "Trehalose: a cryoprotectant that enhances recovery and preserves function of human pancreatic islets after long-term storage." Diabetes 46(3): 519-23; Eroglu A M J, Russo R, Bieganski A, Fowler S, Cheley H B and Toner M, 2000. "Intracellular trehalose improves the survival of cryopreserved mammalian cells." Nat Biotechnol 18(2): 163-167) are often used in combination with DMSO as adjuncts in freezing media to increase the recovery of viable cells. These large mol. wt. substances protect the cell by facilitating intra-cellular dehydration through diffusion of water out of the cell via osmotic forces and inhibition of ice-crystal formation. At Eli Lilly & Company, the freezing medium composed primarily of a plant derived peptone and 10% (v/v) synthetic glycerin.

Our basal medium has glucose and other large-molecular-weight membrane non-permeating solutes like such as sucrose, trehalose, raffinose, etc. may come from plant's extract. Veg peptone like soya peptone has high carbohydrate (total 24%) e.g. raffinose, sucrose and various other reducing sugars and yeast extract also has about 17.5% total carbohydrate.

It is clear that this medium appears to provide measure of protection during freezing and thawing as judged by viability and re-growth potential of promastigotes. Cryoprotective nature of the medium might be due to collective effects of known cryoprotectants present in the medium as medium supplements. However, this medium allows the storage of *L. donovani* isolates in liquid nitrogen for considerable periods (at least one and half year) without extra expenses and regulatory risks/issues, as the case with animal derived products. Further, cells from *Leishmania*-Bank do not need to undergo stringent tests for safety, including tests that screen for infectious agents. So, the costs associated with use of such cells will increase much. This is not in prior art.

EXAMPLE-12

Determination of Infectivity of Promastigotes:

Previous studies suggest that factors such as culture medium (Neal R A, 1984. *Leishmania* major: culture media, mouse strains, and promastigotes virulence and infectivity. Exp. Parasitol. 57 (3): 269-273; O'Daly J A and Rodriguez M B, 1988. Differential growth requirements of several *Leishmania* spp. In chemically defined culture media. Acta Trop. 45(2): 109-126; Merlen T, Sereno D, Brajon N, Rostand F and Lemesre J L, 1999. *Leishmania* spp: completely defined medium without serum and macromolecules (CDM/LP) for the continuous in-vitro cultivation of infective promastigotes forms. Am. J. Trop. Med. Hyg. 60: 41-50; Dey T, Afrin F, Anam K and Ali N, 2002. Infectivity and virulence of *Leishmania donovani* promastigotes: a role for media, source, and strain of parasite. J. Eukaryote Microbiol. 49 (4): 270-274), medium of primary isolation (Neal R A, 1984. *Leishmania major*: culture media, mouse strains, and promastigotes virulence and infectivity. Exp. Parasitol. 57 (3): 269-273), growth phases, number of sub-passages (Giannini M S, 1974. Effects of promastigotes growth, frequency of subculture, and host age on promastigotes—initiated infections with *Leishmania donovani* in the golden hamster. J. Protozool. 21 (4), 521-527; Semprevivo L H, Yusuf, J N various laboratory procedures. Zeitschrift fur Parasitenkunde 65, 43-51; Nolan T J and Herman R, 1985. Effects of long-term in vitro cultivation on *Leishmania donovani* promastigotes. J Protozool. 32(1): 70-75), animal's species/strain and their age, sex, inoculum size (Mbati P A, Abok K, Orago A S, Anjili C O, Githure J I, Kagai J M and Koech D K, 1994. Establishment of an appropriate inoculum dose of *Leishmania donovani* promastigotes required to establish a visceral infection in laboratory animal rodent models. Afr. J. Health Sci. 1(4): 165-168), route of inoculation etc affect the establishment of parasites in animal model. Infectivity studies showed that *L. major* promastigotes grown in Schneider's medium maintained infectivity to BALB/c mice throughout the period of cultivation. Infectivity to CD1 strain mice was progressively lost. Promastigotes grown in blood agar medium, however, lost infectivity to both strains of mice at a faster rate than promastigotes grown in Schneider's medium (Neal R A, 1984. *Leishmania major*: culture media, mouse strains, and promastigotes virulence and infectivity. Exp. Parasitol. 57(3): 269-73). Schlein & Jacobson (Schlein Y and Jacobson R L, 1994. Mortality of *Leishmania major* in *Phlebotomus papatasi* caused by plant feeding of the sand flies. Am. J. Trop. Med. Hyg. 50:20-27) observed that haemoglobin or blood in the growth medium of *L. major* inhibited the formation of infective promastigotes. Inoculation of mice with stationery-phase parasites from control medium caused infections in 20/29 mice, compared to 3/20 mice injected with parasites grown with rabbit hemoglobin.

Hence, for developing a new medium for continuous cultivation of *Leishmania* promastigotes, it is worthwhile to check the length of time/number of sub-passage that could maintain the infectivity. The freshly transformed *Leishmania* promastigotes gradually lose their infectivity due to prolonged in vitro cultivation.

To determine the infectivity of promastigotes cultured in this nutritionally changed/modified growth environment having plant origin based supplement, 1 (VL) primary isolate was successively sub-passaged during log phase in LGPY medium supplemented with 2 different plants' extract (20%, v/v) whist LGPY with peptone of animal origin medium supplemented with 10% FCS was taken as control.

Promastigotes of stationery phase from both the media groups were harvested by centrifugation at 2500 rpm for 20 minutes at 4° C. and washed with sterile Locke's solution (pH 7.2). Rosettes of promastigotes were dispersed by agitating through laboratory shaker. Inbred male BALB/c mice (6 to 8 week old, weighing about 20 g+2 g) were distributed into two groups of 3 animals in each for experiment. Promastigotes were inoculated ($1\times10^8$ cells/animal) intraperitoneally from sub-passage number 8. Animals were maintained on commercial pellet food and given water ad libitum.

To determine the infectivity of promastigotes in spleen, animals from both groups were sacrificed in 3 months. Spleen was removed aseptically. Small pieces (minced) of spleen were inoculated in BHI Agar with 30% defibrinated rabbit blood (slant of ca. 3-5 ml) having Locke's solution as overlay (ca. 0.5-1 ml) and Schneider's insect medium with 20% FCS and 10% rabbit blood. Inoculated vials were incubated at 24° C.±1° C. and examined for promastigotes after 4-5 days followed by every 1-2 days interval up to 21 days to say negative. Impression smears from the cut surfaces of the spleen were prepared and fixed with methanol. Smear was microscopically examined after staining with Giemsa for presence of amastigotes.

Spleen was found positive for *Leishmania* parasites i.e. presence of amastigotes/promastigotes. These results demonstrate, unquestionably, that the promastigotes forms of the visceral leishmaniasis as obtained according to the invention are infectious in vivo means able to transform into amastigotes forms, survive, and multiply intracellularly, and retain infectivity in susceptible animal after certain (at least 8) successive sub-passaging.

For parasites causing both cutaneous and visceral leishmaniasis, Merlen et al. (Merlen T, Sereno D, Brajon N, Rostand F and Lemesre J L, 1999. *Leishmania* spp: completely defined medium without serum and macromolecules (CDM/LP) for the continuous in-vitro cultivation of infective promastigotes forms. Am. J. Trop. Med. Hyg. 50: 41-50) found that the absence of serum, proteins, and peptides in their completely defined culture medium (CDM/CP) did not markedly change their in vitro infectivity for resident mouse macrophages and their virulence in animals compared with parasites cultivated in non defined medium. Infectivity studies in hamsters and BALB/c mice showed that promastigotes isolated in biphasic M199 with 10% FCS were several folds more infective than those obtained from M199 with 10% FCS. The medium used for the conversion of amastigotes to promastigotes plays a major role in determining the infectivity of the freshly transformed *L. donovani* promastigotes in hamsters and BALB/c mice (Dey T, Afrin F, Anam K and Ali N, 2002. Infectivity and virulence of *Leishmania donovani* promastigotes: a role for media, source, and strain of parasite. J. Eukaryot. Microbiol. 49(4): 270-274).

EXAMPLE-13

Determination of Capability for Transformation of Amastigotes to Promastigotes:

The medium suitable for maintenance of promastigotes may not be necessarily suitable for primary isolation of promastigotes.

Hence, to determine the capability for transformation of amastigotes to promastigotes clinical material was inoculated in LGPY medium with 20% different plants' extract (code no. 5, 16, 26, 29, 44, 48). Inoculated culture was placed in B.O.D incubator at 25° C.±1° C. After every 1-2 days, a wet smear was examined over 3-4 weeks under the light microscope for presence of motile promastigotes before considered as a negative. Promastigotes were found in this culture medium. Hence, the medium is proved to be capable for transformation of amastigotes to promastigotes.

EQUIVALENTS

While this disclosures has been described and illustrated using certain specific embodiments, it will be understood that further modifications may be made and this application covers any variations, uses, or adaptations of the disclosed embodiments following, in general, the principles/processes of the invention and including such departures from the present disclosure as come within known or customary practice within the art to which the invention pertains and as may be applied to the features herein and as follows in the spirit or scope of the appended claims.

To avoid detail not necessary to enable those skills of art to practice the invention, the description omits certain information known to those skilled in the art. The preceding detailed description as well as claims are, therefore, not to be taken in a limiting sense.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated herein by reference.

We claim:

1. A culture medium for cultivation of *Leishmania* promastigotes, comprising at least one plant extract obtained from a plant selected from the group consisting of *Citrus maxima, Thevetia peruviana, Croton bonplandianum, Benincasa hispida, Dolichos lablab, Calotropis procera, Colocasia esculenta, Amorphophallus paeoniifolius, Coccinia cordifolia, Amaranthus dubius, Citrus aurantifelia, Cucurbita pepo, Sesbania sesban, Solanum melongena, Abutilon indicum, Trianthema portulacastrum*, and *Basella alba* wherein said culture medium is serum-free or animal product-free; and an inorganic salt selected from the group consisting of sodium chloride, potassium chloride, potassium dihydrogen phosphate and calcium chloride.

2. The culture medium as claimed in claim 1, further comprising an organic constituent comprising glucose and yeast extract.

3. The culture medium as claimed in claim 1, wherein the inorganic salts are in the following amounts:

| | |
|---|---|
| Sodium Chloride | 8 g/l |
| Potassium Chloride | 200 mg/l |
| Potassium dihydrogen phosphate | 300 mg/l and |
| Calcium chloride | 200 mg/l, and further comprising 5 g/l of glucose, 5 g/l of yeast, and 10 g/l of |
| Peptone/hydrolysate and Plant extract. | |

4. The culture medium as claimed in claim 3, wherein said plant extract is present in 5 to 20% by weight.

5. The culture medium as claimed in claim 1, for the transformation of amastigotes to promastigotes.

6. A culture medium for cultivation of *Leishmania* promastigotes, comprising at least one plant extract obtained from a plant selected from the group consisting of *Citrus maxima, Thevetia peruviana, Croton bonplandianum, Benincasa hispida, Dolichos lablab, Calotropis procera, Colocasia esculenta, Amorphophallus paeoniifolius, Coccinia cordifolia, Amaranthus dubius, Citrus aurantifelia, Cucurbita pepo, Sesbania sesban, Solanum melongena, Abutilon indicum, Trianthema portulacastrum*, and *Basella alba* wherein said culture medium is serum-free or animal product-free; and an organic constituent comprising glucose and yeast extract.

7. The culture medium as claimed in claim 6, further comprising an inorganic salt selected from the group consisting of sodium chloride, potassium chloride, potassium dihydrogen phosphate and calcium chloride, wherein the inorganic salts are in the following amounts:

Sodium Chloride 8 g/l Potassium Chloride 200 mg/l Potassium dihydrogen phosphate 300 mg/l, and Calcium chloride 200 mg/l, and further comprising 5 g/l of glucose, 5 g/l of yeast extract, and 10 g/l of Peptone/hydrolysate and Plant extract.

8. The culture medium as claimed in claim 7, wherein said plant extract is present in 5 to 20% by weight.

9. The culture medium as claimed in claim 6, for the transformation of amastigotes to promastigotes.

* * * * *

UNITED STATES PATENT AND TRADEMARK OFFICE
CERTIFICATE OF CORRECTION

| | | |
|---|---|---|
| PATENT NO. | : 9,909,100 B2 | Page 1 of 1 |
| APPLICATION NO. | : 14/770984 | |
| DATED | : March 6, 2018 | |
| INVENTOR(S) | : Pradeep Das et al. | |

It is certified that error appears in the above-identified patent and that said Letters Patent is hereby corrected as shown below:

On the Title Page

Column 2, Item (57) ABSTRACT, Line 3, delete "peptone/hydrolystate" and insert -- peptone/hydrolysate --

In the Claims

Column 28, Line 8, Claim 1, delete "aurantifelia," and insert -- aurantifolia, --

Column 28, Line 21, Claim 3, delete "8 g/1" and insert -- 8 g/l --

Column 28, Line 22, Claim 3, delete "200 mg/1" and insert -- 200 mg/l --

Column 28, Line 23, Claim 3, delete "300 mg/1" and insert -- 300 mg/l --

Column 28, Line 24, Claim 3, delete "200 mg/1" and insert -- 200 mg/l --

Column 28, Line 25, Claim 3, delete "5 g/1" and insert -- 5 g/l --

Column 28, Line 26, Claim 3, delete "5 g/1" and insert -- 5 g/l --

Column 28, Line 26, Claim 3, delete "yeast," and insert -- yeast, extract, --

Column 28, Line 26, Claim 3, delete "10 g/1" and insert -- 10 g/l --

Column 28, Line 39, Claim 6, delete "aurantifelia," and insert -- aurantifolia, --

Signed and Sealed this
Twenty-second Day of May, 2018

Andrei Iancu
*Director of the United States Patent and Trademark Office*